United States Patent
Black et al.

[11] Patent Number: 5,733,909
[45] Date of Patent: Mar. 31, 1998

[54] DIPHENYL STILBENES AS PRODRUGS TO COX-2 INHIBITORS

[75] Inventors: Cameron Black, Pointe Claire; Mario Girard, Montreal; Daniel Guay, Ile Perrot; Zhaoyin Wang, Pierrefonds, all of Canada

[73] Assignee: Merck Frosst Canada, Inc., Kirkland, Canada

[21] Appl. No.: 784,663

[22] Filed: Jan. 21, 1997

Related U.S. Application Data

[60] Provisional application No. 60/010,950, Feb. 1, 1996.

[51] Int. Cl.$^6$ .......... A01N 41/10; A61K 31/535; C07C 311/29
[52] U.S. Cl. .......... 514/238.8; 514/534; 514/544; 514/562; 514/570; 514/571; 514/604; 514/699; 514/710; 544/158; 558/411; 560/11; 560/12; 562/429; 562/430; 564/88; 564/89; 568/23
[58] Field of Search .......... 514/238.8, 534, 514/544, 562, 570, 571, 604, 699, 710; 544/158; 558/411; 560/11, 12; 562/429, 430; 564/88, 89; 568/23

[56] References Cited

U.S. PATENT DOCUMENTS 5,393,790  2/1995  Reitz et al. .......... 514/709

FOREIGN PATENT DOCUMENTS 0 424 541 A1  5/1991  European Pat. Off. .
WO 95/00501  1/1995  WIPO .

*Primary Examiner*—Robert W. Ramsuer
*Assistant Examiner*—Jane C. Oswecki
*Attorney, Agent, or Firm*—Richard C. Billups; David L. Rose

[57] ABSTRACT

The invention encompasses the novel compound of Formula I useful in the treatment of cyclooxygenase-2 mediated diseases.

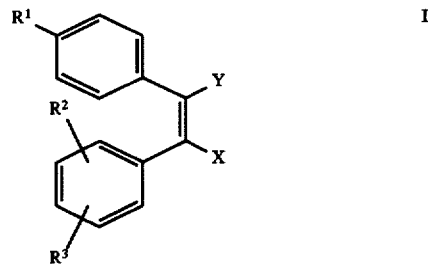

The invention also encompasses certain pharmaceutical compositions for treatment of cyclooxygenase-2 mediated diseases comprising compounds of Formula I.

14 Claims, No Drawings

DIPHENYL STILBENES AS PRODRUGS TO COX-2 INHIBITORS

This application claims the benefit of Provisional Application No. 60/010,950, Feb. 01, 1996.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

A number of stilbene derivatives are known in the chemical literature. Toda et al., in Chem. Commun. 1234–5 (1984) describe the dialdehydes A and the diol B is described by Tsuji et al., *J. Am. Chem. Soc.* 88, 1289–92 (1966), and diol C was prepared by Dhawan et al., *J. Org. Chem.*, 45, 922–4 (1980). No utility is disclosed for these compounds, nor do they carry the R1 substituent of the present invention.

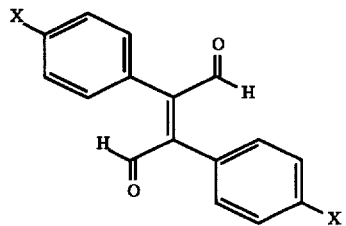

A
X = H or Cl

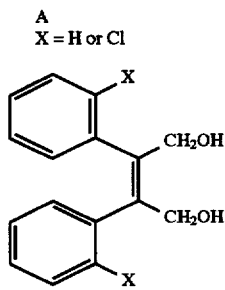

B X = H Tsuji
C X = Cl Dhawan

Structure D is disclosed as having usefulness for treating hyperlipidemia by Hashimoto et at., European Patent Application 424,541 (May 2, 1991).

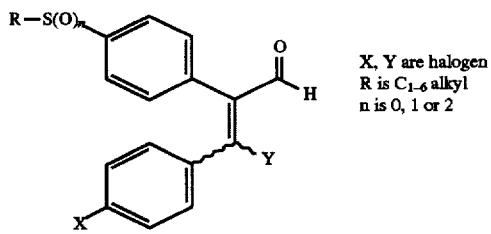

D

X, Y are halogen
R is $C_{1-6}$ alkyl
n is 0, 1 or 2

These compounds (D) lack the second carbon substituent X of the present invention and have an unrelated utility.

SUMMARY OF THE INVENTION

The invention encompasses the novel compound of Formula I as well as a method of treating COX-2 mediated diseases comprising administration to a patient in need of such treatment of a non-toxic therapeutically effective amount of a compound of Formula I. These compounds are prodrugs of compounds which inhibit COX-2 selectively over COX-1. The prodrugs are converted in vivo to the selective inhibitors.

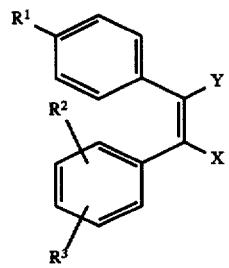

I

The invention also encompasses certain pharmaceutical compositions for treatment of COX-2 mediated diseases comprising compounds of Formula I.

DETAILED DESCRIPTION OF THE INVENTION

In one embodiment, the invention encompasses the novel compound of Formula I as well as a method of treating COX-2 mediated diseases comprising administration to a patient in need of such treatment of a non-toxic therapeutically effective amount of a compound of Formula I

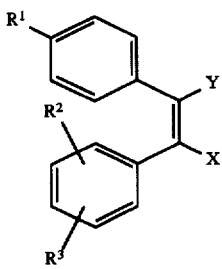

I or pharmaceutically acceptable salts thereof wherein

X is
(a) $CH_2OH$,
(b) CHO,
(c) $CO_2R^4$, or
(d) $CONR^4{}_2$;

Y is
(a) $CH_3$, or
(b) $CH_2OR^5$;

$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$;

$R^2$ and $R^3$ each are independently selected from the group consisting of
(a) hydrogen,
(b) halo,
(c) $C_{1-6}$alkoxy,
(d) $C_{1-6}$alkylthio,
(e) CN,
(f) $CF_3$,
(g) $C_{1-6}$alkyl, and
(h) $N_3$;

$R^4$ is selected from the group consisting of
(a) hydrogen,
(b) $C_{1-6}$alkyl, and
(c) mono- or disubstituted benzyl wherein the substituent is selected from
(1) hydrogen,
(2) halo,
(3) $C_{1-6}$alkyl,
(4) $C_{1-6}$alkoxy,
(5) $C_{1-6}$alkylthio,
(6) OH,
(7) CN, and
(8) $CF_3$, or two $R^4$ groups joined to the same N can form a saturated 5, 6 or 7-membered ring optionally containing an O or S or an additional N atom, said N atom substituted by a hydrogen or $C_{1-6}$ alkyl;

$R^5$ is selected from the group consisting of
(a) $C_{1-6}$alkyl, (b) mono- or disubstituted benzyl wherein the substituent is selected from
(1) hydrogen,
(2) halo,
(3) $C_{1-6}$alkyl,
(4) $C_{1-6}$alkoxy,
(5) $C_{1-6}$alkylthio,
(6) OH,
(7) CN,
(8) $CF_3$, and
(9) $CO_2R^4$.

In one genus, preferred compounds within this embodiment are those wherein $R^1$ is selected from the group consisting of
(a) $S(O)_2CH_3$, and
(b) $S(O)_2NH_2$;

$R^2$ and $R^3$ are each independently selected from the group consisting of
(1) hydrogen,
(2) halo, selected from the group consisting of fluoro, chloro and bromo.

In another genus, preferred compounds within this embodiment are those wherein

Y is $CH_3$ or $CH_2OC_{1-6}$alkyl.
Within this genus is the class of compounds wherein Y is $CH_3$ or $CH_2OC_{1-6}$alkyl;
R1 is selected from the group consisting of
(a) $S(O)_2CH_3$,
(b) $S(O)_2NH_2$,
(c) $S(O)_2NHC(O)CF_3$,
(d) $S(O)NHCH_3$,
(e) $S(O)NHNH_2$, and
(f) $S(O)NHNHC(O)CF_3$; and $R^2$ and $R^3$ are each independently selected from the group consisting of
(a) hydrogen,
(b) fluoro, chloro, and bromo,
(c) $C_{1-4}$alkoxy,
(d) $C_{1-4}$alkylthio,
(e) CN,
(f) $CF_3$, and
(g) $C_{1-4}$alkyl.

Within this class is the sub-class of compounds wherein $R^2$ and $R^3$ are each independently selected from the group consisting of
(1) hydrogen, and
(2) halo;

$R^4$ is hydrogen or methyl; and
$R^5$ is $C_{1-6}$alkyl.

In another genus, preferred compounds within the above embodiment are those wherein X is $CO_2R^4$.
Within this genus is the class of compounds wherein
X is $CO_2R^4$;
Y is methyl or $CH_2OR^5$;
$R^1$ is $S(O)_2CH_3$;
$R^2$ and $R^3$ each are independently selected from the group consisting of
(a) hydrogen, and
(b) halo;

$R^4$ is selected from the group consisting of
(a) hydrogen, and
(b) $C_{1-6}$alkyl, $R^5$ is selected from the group consisting of (a) $C_{1-6}$alkyl,
(b) mono- or disubstituted benzyl wherein the substituent is selected from
  (1) hydrogen,
  (2) halo,
  (3) $C_{1-6}$alkoxy, and
  (4) OH.

Within this class is the sub-class of compounds wherein

X is $CO_2R^4$;

Y is methyl or $CH_2OR^5$;

$R^1$ is $S(O)_2CH_3$;

$R^2$ and $R^3$ each are independently selected from the group consisting of
(a) hydrogen, and
(b) halo;

$R^4$ is selected from the group consisting of
(a) hydrogen, and
(b) $C_{1-6}$alkyl, $R^5$ is selected from the group consisting of
(a) $C_{1-6}$alkyl,
(b) mono- or disubstituted benzyl wherein the substituent is selected from
  (1) hydrogen,
  (2) halo,
  (3) $C_{1-6}$alkoxy, and
  (4) OH.

Illustrating the invention are the compounds of Tables II and III.

For purposes of this specification alkyl is defined to include linear, branched, and cyclic structures, with the indicated number of carbon atoms. Examples of alkyl are methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly alkoxy and alkylthio means linear, branched and cyclic structures with the indicated number of carbon atoms.

For purposes of this specification, where a definition appears twice, such as "$R^4$" in "$CONR^4_2$," each occurance is to be considered independent of each other occurance. Thus, in "$CONR^4_2$", the "$R^4$" groups need not be identical.

For purposes of this specification Halo means F, Cl, Br, or I.

The following abbreviations have the indicated meanings:

AA = arachidonic acid
Ac = acetyl
AIBN = 2,2–azobisisobutyronitrile
Bn = benzyl
CHO = chinese hamster ovary
CMC = 1-cyclohexyl-3-(2-morpholinoethyl) carbodiimidemetho-p-toluenesulfonate
COX = cyclooxygenase
DBU = diazabicyclo[5.4.0]undec-7-ene
DMAP = 4-(dimethylamino)pyridine
DMF = N,N-dimethylformamide
DMSO = dimethyl sulfoxide
$Et_3N$ = triethylamine
HBSS = Hanks balanced salt solution
HEPES = N-[2-Hydroxyethyl]piperazine-$N^1$–[2-ethanesulfonic acid]
HWB = human whole blood
KHMDS = potassium hexamethyldisilazane
LDA = lithium diisopropylamide
LPS = lipopolysaccharide
mCPBA = metachloro perbenzoic acid
MMPP = magnesium monoperoxyphthalate
Ms = methanesulfonyl = mesyl
MsO = methanesulfonate = mesylate
NBS = N-bromosuccinimide -continued NCS = N-chlorosuccinimide
NIS = N-iodosuccinimide
NSAID = non-steroidal anti-inflammatory drug
Oxone ® = potassium peroxymonosulfate
PCC = pyridinium chlorochromate
PDC = pyridinium dichromate
r. t. = room temperature
rac. = racemic
Tf = trifluoromethanesulfonyl = triflyl
TFAA = trifluoroacetic anhydride
TfO = trifluoromethanesulfonate = triflate
THF = tetrahydrofuran
TLC = thin layer chromatography
TMPD = N,N,N',N'-tetramethyl-p-phenylenediamine
Ts = p-toluenesulfonyl = tosyl
TsO = p-toluenesulfonate = tosylate
Tz = 1H(or 2H)-tetrazol-5-yl
$SO_2Me$ = methyl sulfone (also $SO_2CH_3$)
$SO_2NH_2$ = sulfonamide Alkyl group abbreviations Me = methyl
Et = ethyl
n-Pr = normal propyl
i-Pr = isopropyl
n-Bu = normal butyl
i-Bu = isobutyl
s-Bu = secondary butyl
t-Bu = tertiary butyl
c-Pr = cyclopropyl
c-Bu = cyclobutyl
c-Pen = cyclopentyl
c-Hex = cyclohexyl Dose Abbreviations bid = bis in die = twice daily
qid = quater in die = four times a day
tid = ter in die = three times a day Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The Compound of Formula I is useful for the relief of pain, fever and intimation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, bums, injuries, following surgical and dental procedures. In addition, such a compound may inhibit cellular neoplastic transformations and metastic tumour growth and hence can be used in the treatment of cancer. Compound 1 may also be of use in the treatment and/or prevention of cyclooxygenase-mediated proliferative disorders such as may occur in diabetic retinopathy and tumour angiogenesis.

Compound I, by virtue of its in vivo conversion to a COX-2 inhibitor, will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis), and for treatment of glaucoma.

The compounds of Formula I are prodrugs of selective COX-2 inhibitors, and exert their action by conversion in vivo to these active and selective COX-2 inhibitors. The active compounds formed from the compounds of the present invention are described in the following documents which are hereby encorporated by reference:

WO 95/00501, published Jan. 5, 1995, WO 95/18799, published Jul. 13, 1995 and U.S. Pat. No. 5,474,995, published Dec. 12, 1995.

In certain respects, compounds of the present invention have advantages over the compounds described in these documents by virtue of improved pharmacokinetic and/or safety profiles. A general description of the advantages and uses of prodrugs as pharmaceutically useful compounds is given in an article by Waller and George in Br. J. Clin. Pharmac. Vol. 28, pp. 497–507, 1989.

By way of illustration, the following compounds of the present invention are converted to the indicated COX-2 selective inhibitors.

other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine,

| Example | Prodrug | Active Drug | Reference |
|---|---|---|---|
| 1 | [structure with SO₂Me, MeO-C(=O)-] | [structure with SO₂Me] | U.S. Pat. No. 5,474,995 |
| 2 | [structure with SO₂Me, NaO-C(=O)-] | [structure with SO₂Me] | U.S. Pat. No. 5,474,995 |
| 3 | [structure with SO₂Me, MeO-C(=O)-, F] | [structure with SO₂Me, F] | U.S. Pat. No. 5,474,995 |

By virtue of its in vivo conversion to a compound with high inhibitory activity against COX-2 and/or a specificity for COX-2 over COX-1, compound I will prove useful as an alternative to conventional NSAID'S, particularly where such non-steroidal antiinflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

The pharmaceutical compositions of the present invention comprise a compound of Formula I as an active ingredient or a pharmaceutically acceptable salt, thereof, and may also contain a pharmaceutically acceptable carrier and optionally morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of the high COX-2 activity and/or specificity for COX-2 of the inhibitor derived from I over COX-1, Compound I will prove useful as an alternative to conventional NSAID's, particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carders, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known an using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed (for purposes of this application, topical application shall include mouth washes and gargles). Topical formulations may generally be comprised of a pharmaceutical carder, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carder materials to produce a single dosage form will vary depending upon the host treated and the particular mode of administration. For example, a formulation intended for the oral administration of humans may contain from 0.5 mg to 5 g of active agent compounded with an appropriate and convenient amount of carder material which may vary from about 5 to about 95 percent of the total composition. Dosage unit forms will generally contain between from about 1 mg to about 500 mg of an active ingredient, typically 25 rag, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods

METHOD A

Treatment of a ketal 1 and a bistrimethylketene acetal 2 with a suitable Lewis acid such as $TiCl_4$ or $Et_2O.BF_3$ in an appropriate solvent such as $CH_2Cl_2$ provides a adduct 3 as a diastereomeric mixture. Esterification of 3 with $CH_2N_2$ followed by treatment with a base such as DBU gives rise to a mixture of 5 and 6 which are separated by silica gel chromatography. Oxidation of 5 with MMPP or mCPBA affords the desired product 7.

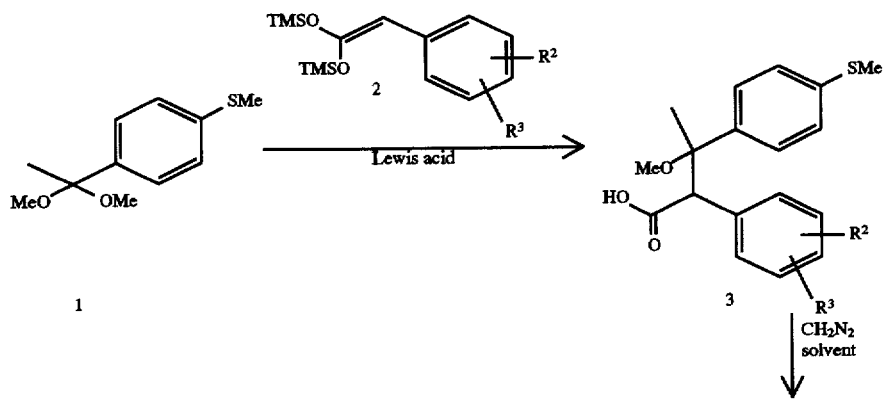

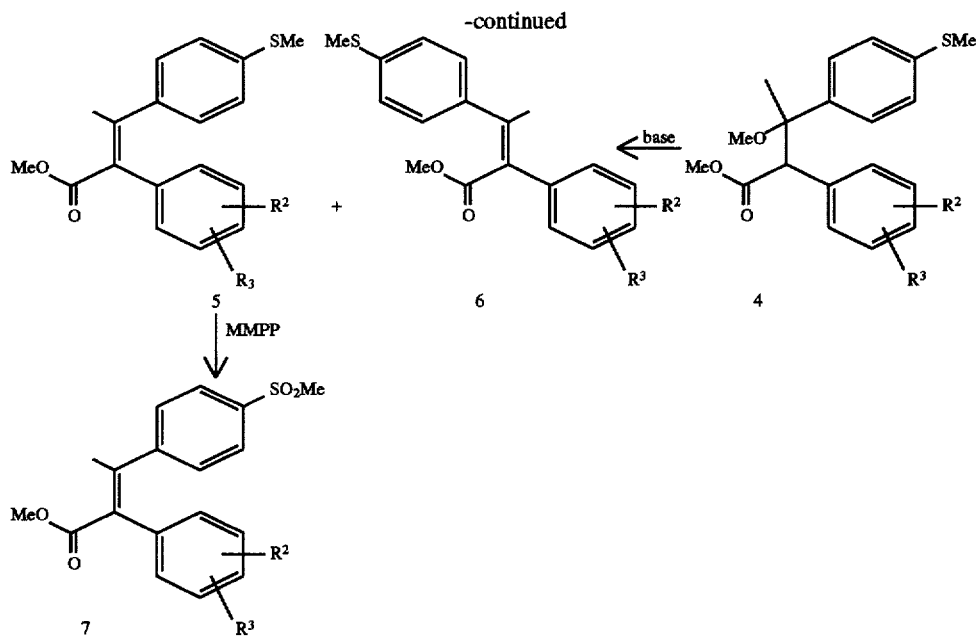

Method B

Hydrolysis of ester 7 with a base such as LiOH or NaOH in a quaeous solvent mixture such as THF/H$_2$O or MeOH/H$_2$O yields the desired carboxlic acid 8.

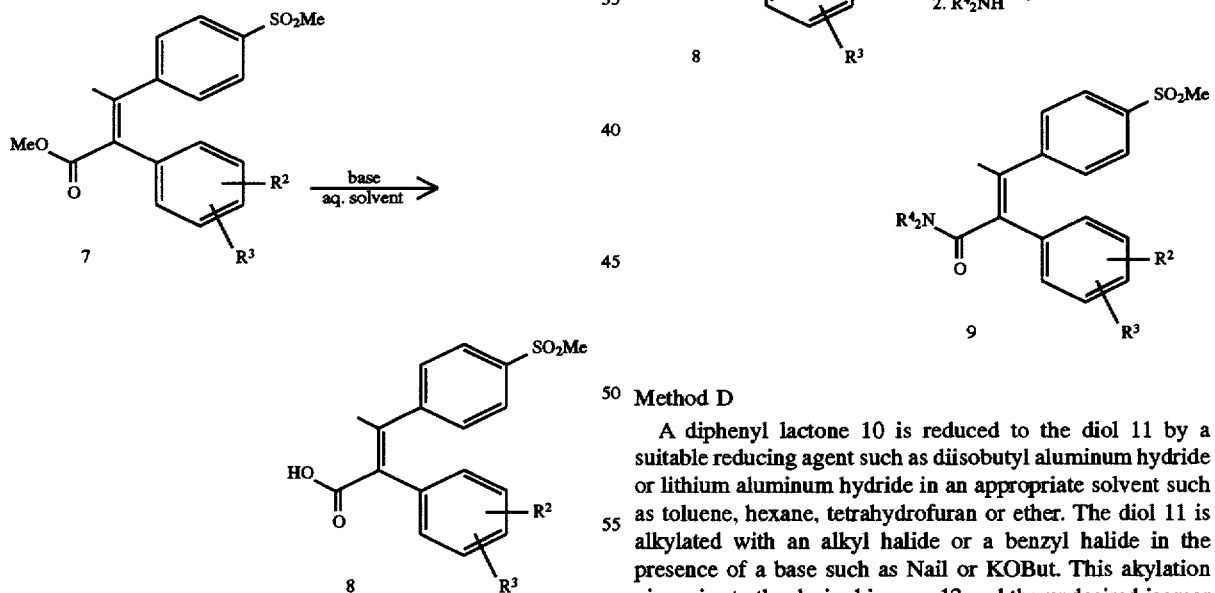

Method C

Treatment of carboxylic acid 8 with oxaly chloride followed by an appropriate amine afford the desired amide 9.

Method D

A diphenyl lactone 10 is reduced to the diol 11 by a suitable reducing agent such as diisobutyl aluminum hydride or lithium aluminum hydride in an appropriate solvent such as toluene, hexane, tetrahydrofuran or ether. The diol 11 is alkylated with an alkyl halide or a benzyl halide in the presence of a base such as NaH or KOBut. This akylation gives rise to the desired isomer 12 and the undesired isomer 13, which are separated by chromatography or crystallization. Compound 12 is oxidized to the aldehyde 14 by a reagent such as manganese dioxide. Further oxidation of 14 with NaClO$_2$ yields acid 15. Alternatively, 12 can be oxidized with Cr$^{+6}$ reagents directly to acid 15. Base treatment of 15 generates the salt 16. Esters 17 can be prepared by reacting 15 with an alkylating agent in the presence of a base. The methyl ester of 15 is conveniently prepared on a small scale by the reaction of 15 with diazomethane in ether.

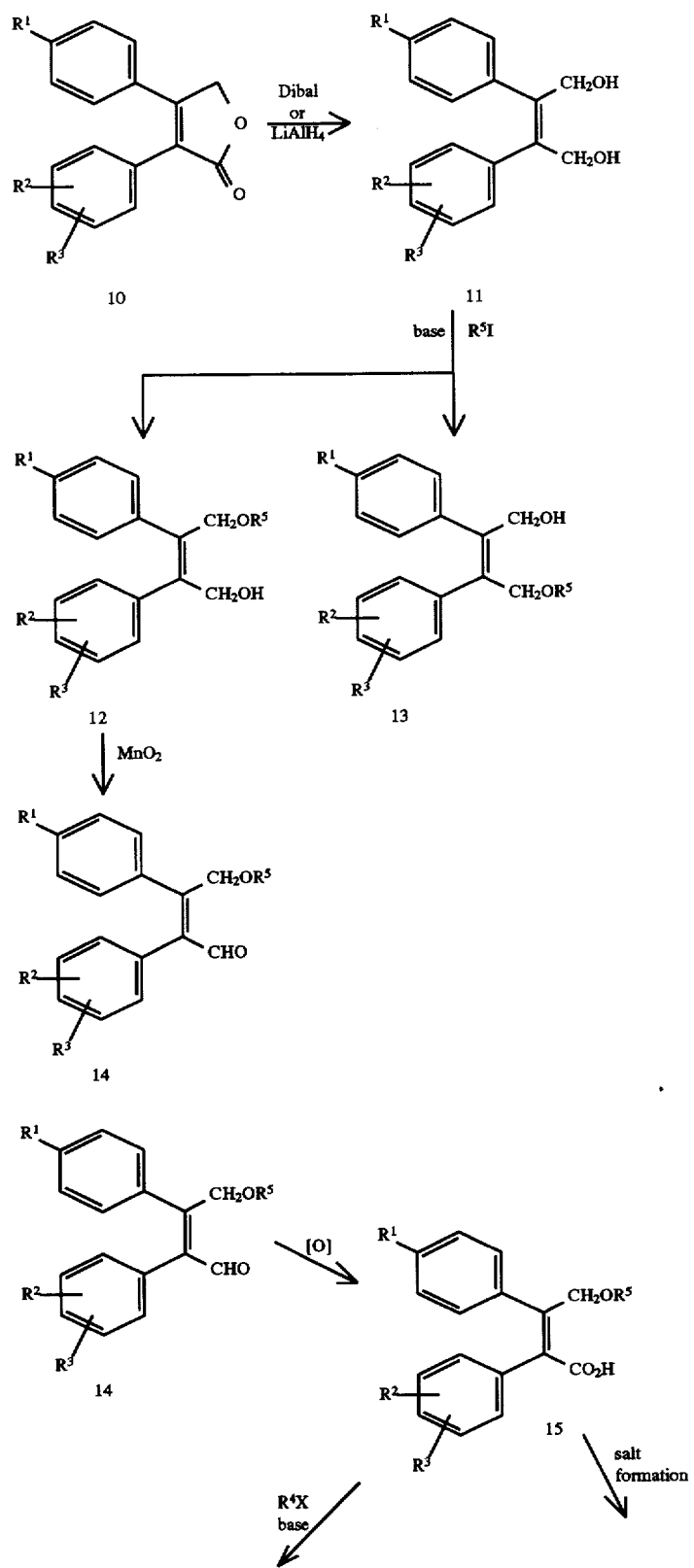

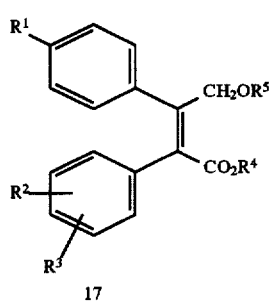

17

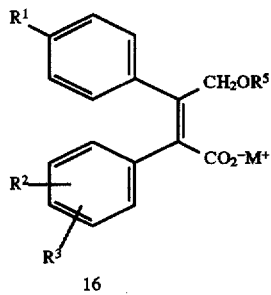

16

$R^4 = C_{1-6}$ alkyl or substituted benzyl

M = Li, Na, K, Mg/2

Method E

A diphenyl maleic anhydride 18 can be reduced to diol 11 with suitable hydride reducing agents such as di-isobutyl aluminum hydride or lithium aluminum hydride. Solvents such as toluene, tetrahydrofuran or ether, or a mixture thereof are suitable for the reduction.

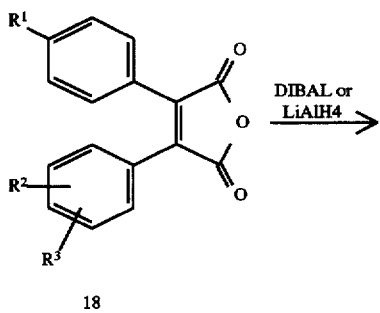

18

DIBAL or LiAlH4 →

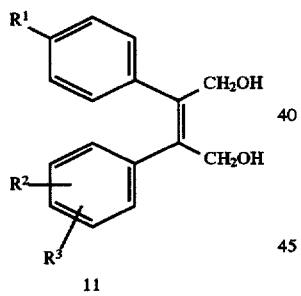

11

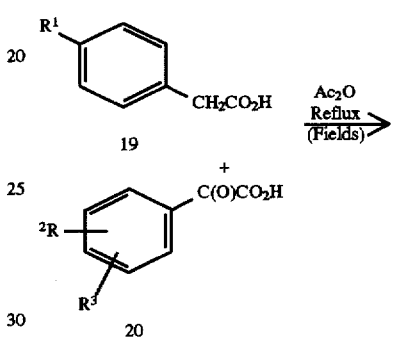

19

Ac₂O
Reflux
(Fields)

+

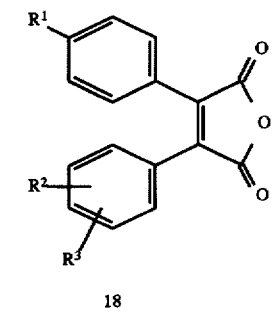

20

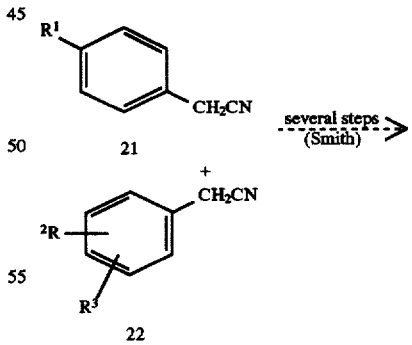

21 several steps
(Smith)

+

22

Method F

The 2,3-diphenyl maleic anhydride 18 can be prepared by the method of Fields [*J. Org. Chem.*, vol. 55, pp. 5165–70 (1990); U.S. Pat. No. 4,596,867] in which a phenylacetic acid 19s made to react with an α-oxophenylacetic acid 20 (preferably as its potassium salt) in refluxing acetic anhydride.

A multi-step sequence to 18 from phenylacetonitriles such as and 22 is described by Smith, et. al., in *J. Org. Chem.*, vol. 55, pp. 3351–62 (1990).

Florac and co-workers in Tetrahedron, vol. 46, pp. 445–52 (1990) describe another synthesis of 18 in several steps from α-bromo phenylaceto hydrazides 23 and 24.

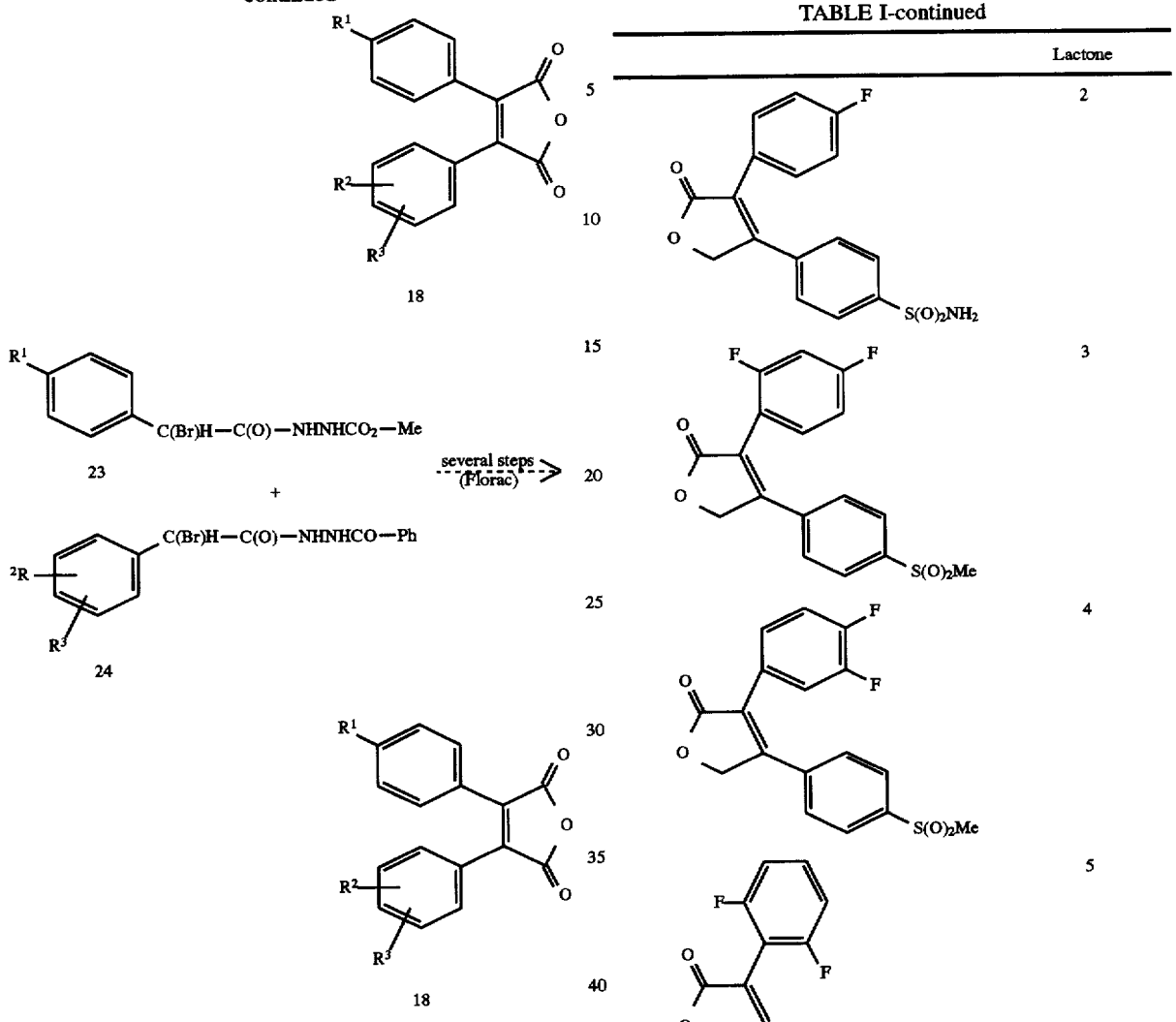
In Table I are shown some lactones 10 from which the compounds of the present invention can be prepared according to Method D.
In Table II and III are shown compounds representative of the present invention (structures Ia and Ib).
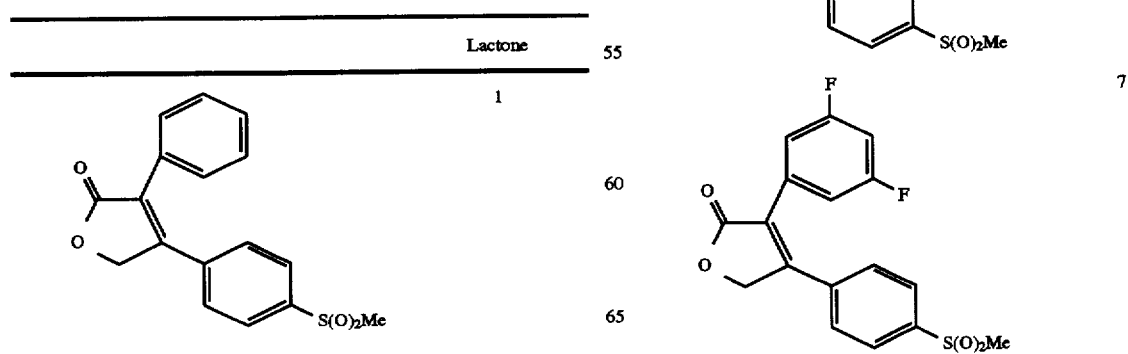

TABLE I-continued

| Structure | Lactone |
|---|---|
| 4-Br-C6H4 / 4-MeSO2-C6H4 lactone | 8 |
| 4-Cl-C6H4 / 4-MeSO2-C6H4 lactone | 9 |
| 4-OMe-C6H4 / 4-MeSO2-C6H4 lactone | 10 |
| 4-F-C6H4 / 4-MeSO2-C6H4 lactone | 11 |
| 2-Cl-C6H4 / 4-MeSO2-C6H4 lactone | 12 |
| 2-Br-4-F-C6H3 / 4-MeSO2-C6H4 lactone | 13 |
| 2-Br-4-Cl-C6H3 / 4-MeSO2-C6H4 lactone | 14 |
| 2-F-4-Cl-C6H3 / 4-MeSO2-C6H4 lactone | 15 |
| 3-Br-4-F-C6H3 / 4-MeSO2-C6H4 lactone | 16 |
| 3-Cl-C6H4 / 4-MeSO2-C6H4 lactone | 17 |
| 2-Cl-4-F-C6H3 / 4-MeSO2-C6H4 lactone | 18 |
| 2,4-Cl2-C6H3 / 4-MeSO2-C6H4 lactone | 19 |

TABLE I-continued

| Structure | Lactone |
|---|---|
| 3,4-diCl-phenyl / 4-S(O)₂Me-phenyl lactone | 20 |
| 2,6-diCl-phenyl / 4-S(O)₂Me-phenyl lactone | 21 |
| 3-Cl-4-F-phenyl / 4-S(O)₂Me-phenyl lactone | 22 |
| 4-CF₃-phenyl / 4-S(O)₂Me-phenyl lactone | 23 |
| 3-F-4-OMe-phenyl / 4-S(O)₂Me-phenyl lactone | 24 |
| 3-Cl-4-OMe-phenyl / 4-S(O)₂Me-phenyl lactone | 25 |
| 3-Br-4-OMe-phenyl / 4-S(O)₂Me-phenyl lactone | 26 |
| 2-F-phenyl / 4-S(O)₂Me-phenyl lactone | 27 |
| 4-SMe-phenyl / 4-S(O)₂Me-phenyl lactone | 28 |
| 3-F-phenyl / 4-S(O)₂Me-phenyl lactone | 29 |
| 2-Cl-6-F-phenyl / 4-S(O)₂Me-phenyl lactone | 30 |
| 3-Br-4-Me-phenyl / 4-S(O)₂Me-phenyl lactone | 31 |

TABLE I-continued

| Structure | Lactone |
|---|---|
| 2-F, 4-Br aryl; 4-S(O)₂Me aryl lactone | 32 |
| 3,4-diBr aryl; 4-S(O)₂Me aryl lactone | 33 |
| 4-Cl, 3-F aryl; 4-S(O)₂Me aryl lactone | 34 |
| 4-Br, 3-F aryl; 4-S(O)₂Me aryl lactone | 35 |
| 2-Cl, 4-Br aryl; 4-S(O)₂Me aryl lactone | 36 |
| 3,4-diCl aryl; 4-S(O)₂NH₂ aryl lactone | 37 |
| 3,4-diF aryl; 4-S(O)₂NH₂ aryl lactone | 38 |
| 4-OMe, 3-Cl aryl; 4-S(O)₂NH₂ aryl lactone | 39 |
| 4-OMe, 3-Br aryl; 4-S(O)₂NH₂ aryl lactone | 40 |
| 4-S(O)₂NH₂ aryl; phenyl lactone | 41 |
| 4-F aryl; 4-S(O)₂NH₂ aryl lactone | 42 |
| 4-S(O)₂NH₂ aryl; 2,4-diF aryl lactone | 43 |

TABLE I-continued

| | Lactone |
|---|---|
| (structure: sulfonamide-phenyl, lactone, 4-chlorophenyl) | 44 |
| (structure: sulfonamide-phenyl, lactone, 2,4-dichlorophenyl) | 45 |
| (structure: sulfonamide-phenyl, lactone, 4-bromophenyl) | 46 |
| (structure: sulfonamide-phenyl, lactone, 2-fluoro-4-bromophenyl) | 47 |

TABLE II

Ia

| COMPOUND | $R^2$ | $R^3$ | X | Y |
|---|---|---|---|---|
| 1 | H | H | $CH_2OH$ | $CH_3$ |
| 2 | H | H | $CH_2OH$ | $CH_2OMe$ |
| 3 | H | H | CHO | $CH_3$ |
| 4 | H | H | $CO_2H$ | $CH_3$ |
| 5 | H | H | $CO_2Me$ | $CH_3$ |

TABLE II-continued

Ia

| COMPOUND | $R^2$ | $R^3$ | X | Y |
|---|---|---|---|---|
| 6 | H | H | $CO_2Na$ | $CH_3$ |
| 7 | H | H | CHO | $CH_2OMe$ |
| 8 | H | H | $CO_2H$ | $CH_2OMe$ |
| 9 | H | H | $CO_2Me$ | $CH_2OMe$ |
| 10 | H | H | $CO_2Na$ | $CH_2OMe$ |
| 11 | H | F | $CH_2OH$ | $CH_3$ |
| 12 | H | F | CHO | $CH_2OMe$ |
| 13 | H | F | $CO_2Me$ | $CH_3$ |
| 14 | H | F | $CO_2H$ | $CH_3$ |
| 15 | H | F | $CO_2Na$ | $CH_3$ |
| 16 | F | F | $CO_2H$ | $CH_3$ |
| 17 | F | F | $CO_2Me$ | $CH_3$ |
| 18 | F | F | $CO_2Me$ | $CH_2OMe$ |
| 19 | F | F | $CO_2Na$ | $CH_2OMe$ |
| 20 | F | F | $CH_2OH$ | $CH_3$ |

TABLE III

Ib

| COMPOUND | $R^2$ | $R^3$ | X | Y |
|---|---|---|---|---|
| 21 | H | H | $CH_2OH$ | $CH_3$ |
| 22 | H | H | $CH_2OH$ | $CH_2OMe$ |
| 23 | H | H | CHO | $CH_3$ |
| 24 | H | H | $CO_2H$ | $CH_3$ |
| 25 | H | H | $CO_2Me$ | $CH_3$ |
| 26 | H | H | $CO_2Na$ | $CH_3$ |
| 27 | H | H | CHO | $CH_2OMe$ |
| 28 | H | H | $CO_2H$ | $CH_2OMe$ |
| 29 | H | H | $CO_2Me$ | $CH_2OMe$ |
| 30 | H | H | $CO_2Na$ | $CH_2OMe$ |
| 31 | H | F | $CH_2OH$ | $CH_3$ |
| 32 | H | F | CHO | $CH_2OMe$ |
| 33 | H | F | $CO_2Me$ | $CH_3$ |
| 34 | H | F | $CO_2H$ | $CH_3$ |
| 35 | H | F | $CO_2Na$ | $CH_3$ |

Assays for determining Biological Activity

The compound of Formula I can be tested using the following assays to determine their cyclooxygenase-2 inhibiting activity.

INHIBITION OF CYCLOOXYGENASE ACTIVITY

Compounds are tested as inhibitors of cyclooxygenase activity in whole cell cyclooxygenase assays. Both of these assays measure prostaglandin $E_2$ synthesis in response to arachidonic acid, using a radioimmunoassay. In these assays, 100% activity is defined as the difference between prostaglandin $E_2$ synthesis in the absence and presence of arachidonate.

Whole Cell Assay

For cyclooxygenase assays, osteosarcoma cells are cultured in 1 mL of media in 24-well multidishes (Nunclon) until confluent ($1-2\times10^5$ cells/well). U-937 cells are grown in spinner flasks and resuspended to a final density of $1.5\times10^6$ cells/mL in 24-well multidishes (Nunclon). Following washing and resuspension of osteosarcoma and U-937 cells in 1 mL of HBSS, 1 µL of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 µL of this diluted solution is added to the cells to give a final arachidonic acid concentration of 10 µM. Control samples are incubated with ethanol vehicle instead of arachidonic acid. Samples are again gently mixed and incubated for a further 10 min. at 37° C. For osteosarcoma cells, reactions are then stopped by the addition of 100 µL of 1N HCl, with mixing and by the rapid removal of the solution from cell monolayers. For U-937 cells, reactions are stopped by the addition of 100 µL of 1N HCl, with mixing. Samples are then neutralized by the addition of 100 µL of 1N NaOH and $PGE_2$ levels measured by radioimmunoassay.

Whole cell assays for COX-2 and COX-1 using CHO transfected cell lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBS S, 15 mM HEPES, pH 7.4, at a cell concentration of $1.5\times10^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells ($0.3\times10^6$ cells in 200 µl) are preincubated with 3 µl of the test drug or DMSO vehicle for 15 min at 37° C. Working solutions of peroxide-free AA (5.5 µM and 110 µM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 µM AA in the CHO[hCOX-1] assay and a final concentration of 10 µM AA in the CHO[hCOX-2] assay. The reaction is terminated by the addition of 10 µl N HCl followed by neutralization with 20 µl of 0.5N NaOH. The samples are centrifuged at 300×g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 cell microsomes

U 937 cells are pelleted by centrifugation at 500×g for 5 min and washed once with phosphate-buffered saline and repelleted. Cells are resuspended in homogenization buffer consisting of 0.1 M Tris-HCl, pH 7.4, 10 mM EDTA, 2 µg/ml leupeptin, 2 µg/ml soybean trypsin inhibitor, 2 µg/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1M Tris-HCl, pH 7.4, 10 mM EDTA to approximately 7 mg protein/ml and stored at –80° C.

Microsomal preparations are thawed immediately prior to use, subjected to a brief sonication, and then diluted to a protein concentration of 125 µg/ml in 0.1M Tris-HCl buffer, pH 7.4 containing 10 mM EDTA, 0.5 mM phenol, 1 mM reduced glutathione and 1 µM hematin. Assays are performed in duplicate in a final volume of 250 µl. Initially, 5 µl of DMSO vehicle or drug in DMSO are added to 20 µl of 0.1M Tris-HCl buffer, pH 7.4 containing 10 mM EDTA in wells of a 96-deepwell polypropylene titre plate. 200 µl of the microsomal preparation are then added and pre-incubated for 15 min at room temperature before addition of 25 µl of 1M arachidonic acid in 0.1M Tris-HCl and 10 mM EDTA, pH 7.4. Samples are incubated for 40 min at room temperature and the reaction is stopped by the addition of 25 µl of 1N HCl. Samples are neutralized with 25 µl of 1N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 µL) contains 100 mM sodium phosphate, pH 6.5, 2 mM genapol X-100, 1 µM hematin, 1 mg/ml gelatin, 80–100 units of purified enzyme (One unit of enzyme is defined as the amount of enzyme required to produce an O.D. change of 0.001/min at 610 nm) and 4 µL of the test compound in DMSO. The mixture is pre-incubated at room temperature (22° C.) for 15 minutes prior to initiation of the enzymatic reaction by the addition of 20 µL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2mL blood aliquot to use as blank (basal levels of $PGE_2$). The remaining blood is incubated with LPS (100 µg/ml final concentration, Sigma Chem, #L-2630 from *E. coli*; diluted in 0.1% BSA (Phosphate buffered saline) for 5 minutes at room temperature. Five hundred µL aliquots of blood are incubated with either 2 µL of vehicle (DMSO) or 2 µL of a test compound at final concentrations varying from 10 nM to 30 µM for 24 hours at 37° C. At the end of the incubation, the blood is centrifuged at 12,000×g for 5 minutes to obtain plasma. A 100 µL aliquot of plasma is mixed with 400 µL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500 µL are immediately transferred to siliconized microcentrifuge tubes preloaded with 2 µL of either DMSO or a test compound at final concentrations varying from 10 nM to 30 µM. The tubes are vortexed and incubated at 37° C. for 1 hour to allow blood to clot. At the end of incubation, serum is obtained by centrifugation (12,000×g for 5 min.). A 100 µL aliquot of serum is mixed with 400 µL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 µl of 1% carrageenan solution in saline (FMC Corp, Maine) into the paw using an insulin syringe with a 25-gauge needle (i.e. 500 µg carrageenan per paw). Three hr later, the paw volume ($V_3$) is measured and the increases in paw volume ($V_3 - V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}$Cr-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37 C. At the end of the incubation, the red blood cells are washed twice with 20 mL HBSS to remove free sodium $^{51}$ chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

RAT PLASMA LEVELS
Per Os Pharmacokinetics in Rats
PROCEDURE

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box is firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.
Vehicles The following vehicles may be used in PO rat blood level determinations:

| | |
|---|---|
| PEG 200/300/400- | restricted to 2 mL/kg |
| Methocel 0.5%–1.0% | 10 mL/kg |
| Tween 80 5% | 10 mL/kg |

Compounds for PO blood levels can be in suspension form. For better dissolution, the solution can be placed in a sonicator for approximately 5 minutes.

Intravenous Pharmacokinetics in Rats
PROCEDURE

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they had lost their righting reflex. The rat is then placed on a restraining board, a nose cone with $CO_2$ delivery is placed over the muzzle and the rat resumed to the board with elastics. With the use of forceps and scissors, the jugular vein is exposed and the zero sample taken, followed by a measured dose of compound which is injected into the jugular vein. Light digital pressure is applied to the injection site, and the nose cone was removed. The time is noted. This constituted the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick to tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.
Vehicles The following vehicles may be used in IV rat blood level determinations:

| | |
|---|---|
| Dextrose: | 1 mL/kg |
| Molecusol 25%: | 1 mL/kg |

DMSO: (Dimethylsulfoxide) Restricted to a dose volume of 0.1 mL per animal

PEG 200: Not more than 60% mixed with 40% sterile water—1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$Cl = \frac{DOSEiv(mg/kg)}{AUCiv}$$

The units of Cl are mL/h.kg (milliliters per hour kilogram)

Representative Biological Data

Compounds of the present invention are prodrugs of inhibitors of COX-2 and are thereby useful in the treatment of COX-2 mediated diseases as enumerated above. The extent of conversion of these compounds to the active COX-2 inhibitors may be seen in the representative results shown below. The plasma levels indicated are the maximum rat plasma concentrations of the active COX-2 inhibitor observed when the rat was treated with a 20 mg/kg oral dose of the indicated prodrug.

TABLE IV

| Example | Plasma Levels (µM)* |
|---|---|
| 1 | 1.0 |

*Maximum plasma concentration of the corresponding lactone observed in rats when dosed at 20 mg/kg orally with the indicated prodrug.

The invention will now be illustrated by the following non-limiting examples in which, unless stated otherwise:

(i) all operations were carded out at room or ambient temperature, that is, at a temperature in the range 18°–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), M.P. (melting point), L (liter(s)), mL (milliliters), g (gram (s)), mg (milligrams(s)), mol (moles), mmol (millimoles), eq (equivalent(s)).

EXAMPLE 1

(E)-3-(4-Methysulfonyl)phenyl-2-phenylbut-2-enoic acid methyl ester

Step 1: 2-Methoxy-3-(4-metylthio)phenyl-2-phenylbutanoic acid methyl ester

To a solution of 1-(1,1-dimethoxyethyl)-4-methylthiobenzene (2.9 g, 13.7 mmol) in 100 mL of $CH_2Cl_2$ cooled at −78° C. was added dropwise a solution of $TiCl_4$ (13.7 mL, 1M in $CH_2Cl_2$), followed by (2,2-bistrimethylsilyloxyvinyl)benzene( 4.6 g, 16.4 mmol, prepared according to the procedure published by Ainsworth, *J. Organomet. Chem.* 1972, 46, 73). The reaction mixture was stirred at −78° C. for 2 h and quenched with pH 7 buffer solution(60 mL, $NaH_2PO_4/Na_2HPO_4$). The mixture was extracted with 3×50 mL of $CH_2Cl_2$. The extracts were combined, dried over $MgSO_4$ and concentrated. The residue was dissolved in 50 mL of ether and treated with an excess of a solution of $CH_2N_2$ in ether. Evaporation of ether provided the crude title compound as a diastereomeric mixture.

Step 2: (E) and (Z)-3-(4-Methylsulfonyl)phenyl-2-phenylbut-2-enoic acid methyl ester The crude product of Step 1(0.62 g) was dissolved in 10 mL of MeOH and cooled to 0° C. A solution of Oxone (4.0 mL, 0.75M in water) was added dropwise and the mixture was stirred at 0° C. for 10 min and at r.t. for 2 h. The mixture was then diluted with water(10 mL) and extracted with 3×20 mL of $CH_2Cl_2$. The extracts were combined, dried over MgSO4 and concentrated. The residue was dissolved in $CH_3CN$(10 mL) and treated with DBU(0.51 mL). The mixture was then heated to reflux for 22 h and cooled to r.t. The solvent was evaporated and the residue was purified by silica gel chromatography. Elution with 9:1 hexane/EtOAc first provided the desired E-isomer(0.25 g) as a white solid.

1H NMR(400 MHz, CDCl4) δ5 7.69 (2H, d), 7.20 (2H, d), 7.11 (3H, m), 6.96 (2H, m), 3.78 (3H, s), 2.97 (3H, s), 2.34 (3H, s).

Continuous elution with 4:1 hexane/EtOAc afforded the Z-isomer (0.35 g) as a white solid.

1H NMR(400 MHz, CDCl3) δ7.92 (2H, d), 7.48 (2H, d), 7.41 (2H, m), 7.33 (3H, m), 3.44 (3H, s), 3.07 (3H, s), 2.01 (3H, s).

EXAMPLE 2

(E)-3-Methylsulfonyl)phenyl-2-phenylbut-2-enoic acid

A mixture of (E)-3-(4-methylsulfonyl)phenyl-2-phenyl-but-2-enoic acid methyl ester (258 mg) and $LiOH.H_2O$ (98 mg) in 5 mL of dioxane and 5 mL of water was heated to reflux for 2 h. The reaction mixture was then cooled to r.t., acidified with 1N HCl to pH~1, and extracted with 50 mL of EtOAc. The EtOAc layer was dried over $Na_2SO_4$ and concentrated. Crystallization from 1:1 hexane/EtOAc afforded the title acid (200 mg) as a white solid.

$^1$H NMR(400 MHz, CDCl$_3$) δ7.69 (2H, d), 7.19 (2H, d), 7.13 (3H, m), 6.98 (2H, m), 2.97 (3H, s), 2.47 (3H, s).

EXAMPLE 3

(E)-2-(4-Fluorophenyl)-3-(4-methylsulfonyl)phenyl-but-2-enoic acid methyl ester $^1$H NMR (400 MHz, acetone-d$_6$) δ7.76 (2H, d), 7.36 (2H, d), 7.06 (2H, m), 6.90 (2H, m), 3.76 (3H, s), 3.05 (3H, s), 2.36 (3H, s).

EXAMPLE 4

(E)-3-(4-Methylsulfonyl)phenyl-1-morpholin-4-yl-2phenylbut-2en-1-one

The title compound was prepared according to the procedures described in Method C.

1H NMR (400 MHz, CDCl$_3$) δ7.73 (2H, d), 7.28 (2H, d), 7.13 (3H, m), 7.01 (2H, m), 3.72 (2H, m), 3.64 (2H, m), 3.42 (4H, bs), 3.00 (3H, s), 2.21 (3H,s).

EXAMPLE 5

(E)-4-Methoxy-3-(4-methylsulfonylphenyl)-2-phenylbutenoic acid

The title compound was prepared according to the procedures described in Method D.

$^1$H NMR (400 MHz, acetone-d$_6$) δ7.75 (2H, m), 7.42 (2H, d), 7.15 (5H, m), 4.55 (2H, s), 3.30 (3H, s), 3.05 (3H, s).

What is claimed is:

1. A compound of Formula I

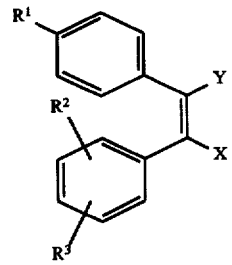

or pharmaceutically acceptable salts thereof wherein

X is
 (a) $CH_2OH$,
 (b) CHO,
 (c) $CO_2R^4$, or
 (d) $CONR^4{}_2$;

Y is (a) $CH_3$, or
(b) $CH_2OR^5$;

$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$;

$R^2$ and $R^3$ each are independently selected from the group consisting of
(a) hydrogen,
(b) halo,
(c) $C_{1-6}$alkoxy,
(d) $C_{1-6}$alkylthio,
(e) CN,
(f) $CF_3$,
(g) $C_{1-6}$alkyl, and
(h) $N_3$;

$R^4$ is selected from the group consisting of
(a) hydrogen,
(b) $C_{1-6}$alkyl, and
(c) mono- or disubstituted benzyl wherein the substituent is selected from
(1) hydrogen,
(2) halo,
(3) $C_{1-6}$alkyl,
(4) $C_{1-6}$alkoxy,
(5) $C_{1-6}$alkylthio,
(6) OH,
(7) CN, and
(8) $CF_3$,
or two $R^4$ groups joined to the same N can form a saturated 5,6 or 7-membered ring optionally containing an O or S or an additional N atom, said N atom substituted by a hydrogen or $C_{1-6}$alkyl;

$R^5$ is selected from the group consisting of
(a) $C_{1-6}$alkyl,
(b) mono- or disubstituted benzyl wherein the substituent is selected from
(1) hydrogen,
(2) halo,
(3) $C_{1-6}$alkyl,
(4) $C_{1-6}$alkoxy,
(5) $C_{1-6}$alkylthio,
(6) OH,
(7) CN,
(8) $CF_3$, and
(9) $CO_2R^4$.

2. A compound according to claim 1 wherein
Y is $CH_3$ or $CH_2OC_{1-6}$alkyl.

3. A compound according to claim 1 wherein
Y is $CH_3$ or $CH_2OC_{1-6}$alkyl;
$R^1$ is selected from the group consisting of
(a) $S(O)_2CH_3$,
(b) $S(O)_2NH_2$,
(c) $S(O)_2NHC(O)CF_3$,
(d) $S(O)NHCH_3$,
(e) $S(O)NHNH_2$, and
(f) $S(O)NHNHC(O)CF_3$; and
$R^2$ and $R^3$ are each independently selected from the group consisting of
(a) hydrogen,
(b) fluoro, chloro, and bromo,
(c) $C_{1-4}$alkoxy,
(d) $C_{1-4}$alkylthio,
(e) CN,
(f) $CF_3$, and
(g) $C_{1-4}$alkyl.

4. A compound according to claim 3 wherein
$R^2$ and $R^3$ are each independently selected from the group consisting of
(1) hydrogen, and
(2) halo;
$R^4$ is hydrogen or methyl; and
$R^5$ is $C_{1-6}$alkyl.

5. A compound according to claim 4 wherein
$R^1$ is selected from the group consisting of
(a) $S(O)_2CH_3$, and
(b) $S(O)_2NH_2$;
$R^2$ and $R^3$ are each independently selected from the group consisting of
(1) hydrogen,
(2) halo, selected from the group consisting of fluoro, chloro and bromo.

6. A compound according to claim 1 wherein
X is $CO_2R^4$.

7. A compound according to claim 6 wherein
X is $CO_2R^4$;
Y is methyl or $CH_2OR^5$;
$R^1$ is $S(O)_2CH_3$;
$R^2$ and $R^3$ each are independently selected from the group consisting of
(a) hydrogen, and
(b) halo;
$R^4$ is selected from the group consisting of
(a) hydrogen, and
(b) $C_{1-6}$alkyl,
$R^5$ is selected from the group consisting of
(a) $C_{1-6}$alkyl,
(b) mono- or disubstituted benzyl wherein the substituent is selected from
(1) hydrogen,
(2) halo,
(3) $C_{1-6}$alkoxy, and
(4) OH.

8. A compound of formula Ia

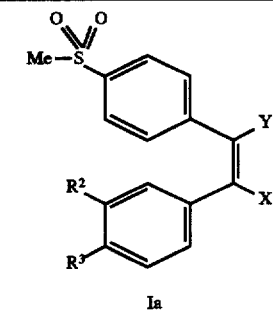

Ia

| wherein | $R^2$ | $R^3$ | X | Y |
|---|---|---|---|---|
| 1 | H | H | $CH_2OH$ | $CH_3$ |
| 2 | H | H | $CH_2OH$ | $CH_2OMe$ |
| 3 | H | H | CHO | $CH_3$ |
| 4 | H | H | $CO_2H$ | $CH_3$ |
| 5 | H | H | $CO_2Me$ | $CH_3$ |
| 6 | H | H | $CO_2Na$ | $CH_3$ |

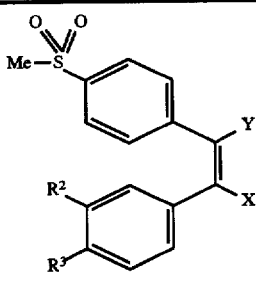

Ia

| wherein | R² | R³ | X | Y |
|---|---|---|---|---|
| 7 | H | H | CHO | CH₂OMe |
| 8 | H | H | CO₂H | CH₂OMe |
| 9 | H | H | CO₂Me | CH₂OMe |
| 10 | H | H | CO₂Na | CH₂OMe |
| 11 | H | F | CH₂OH | CH₃ |
| 12 | H | F | CHO | CH₂OMe |
| 13 | H | F | CO₂Me | CH₃ |
| 14 | H | F | CO₂H | CH₃ |
| 15 | H | F | CO₂Na | CH₃ |
| 16 | F | F | CO₂H | CH₃ |
| 17 | F | F | CO₂Me | CH₃ |
| 18 | F | F | CO₂Me | CH₂OMe |
| 19 | F | F | CO₂Na | CH₂OMe |
| 20 | F | F | CH₂OH | CH₃ |

9. A compound of formula Ib

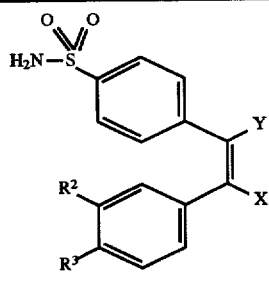

Ib

| wherein | R² | R³ | X | Y |
|---|---|---|---|---|
| 1 | H | H | CH₂OH | CH₃ |
| 2 | H | H | CH₂OH | CH₂OMe |
| 3 | H | H | CHO | CH₃ |
| 4 | H | H | CO₂H | CH₃ |
| 5 | H | H | CO₂Me | CH₃ |
| 6 | H | H | CO₂Na | CH₃ |
| 7 | H | H | CHO | CH₂OMe |
| 8 | H | H | CO₂H | CH₂OMe |
| 9 | H | H | CO₂Me | CH₂OMe |
| 10 | H | H | CO₂Na | CH₂OMe |
| 11 | H | F | CH₂OH | CH₃ |
| 12 | H | F | CHO | CH₂OMe |
| 13 | H | F | CO₂Me | CH₃ |

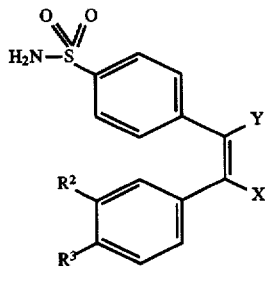

Ib

| wherein | R² | R³ | X | Y |
|---|---|---|---|---|
| 14 | H | F | CO₂H | CH₃ |
| 15 | H | F | CO₂Na | CH₃ |

10. A compound according to claim 1 selected from
(a) (E)-3-(4-Methylsulfonyl)phenyl-2-phenylbut-2-enoic acid methyl ester,
(b) (E-)3-(4-Methylsulfonyl)phenyl-2-phenylbut-2-enoic acid,
(c) (E)-2-(4-Fluorophenyl)-3-(4-methylsulfonyl)phenyl-but-2-enoic acid methyl ester,
(d) (E)-3-(4-Methylsulfonyl)phenyl-1-morpholin-4-yl-2-phenylbut-2-en-1-one, and
(e) (E) -4-Methoxy-3-(4-methylsulfonylphenyl)-2-phenylbutenoic acid.

11. A pharmaceutical composition for treating an inflammatory disease susceptable to treatment with an non-steroidal anti-inflammatory agent comprising:
   a non-toxic therapeutically effective amount of a compound according to claim 1 and a pharmaceutically acceptable carrier.

12. A pharmaceutical composition for treating cyclooxygenase mediated diseases advantageously treated by an active agent that selectively inhibits COX-2 in preference to COX-1 comprising:
   a non-toxic therapeutically effective amount of a compound according to claim 1 and a pharmaceutically acceptable carrier.

13. A method of treating an inflammatory disease susceptable to treatment with an non-steroidal anti-inflammatory agent comprising:
   administration to a patient in need of such treatment of a non-toxic therapeutically effective amount of a compound according to claim 1 and a pharmaceutically acceptable carrier.

14. A method of treating cyclooxygenase mediated diseases advantageously treated by an active agent that selectively inhibits COX-2 in preference to COX-1 comprising:
   administration to a patient in need of such treatment of a non-toxic therapeutically effective amount of a compound according to claim 1.

* * * * *